United States Patent
Ayala et al.

(10) Patent No.: US 7,831,011 B2
(45) Date of Patent: Nov. 9, 2010

(54) COMPUTED TOMOGRAPHY METHOD AND SYSTEM

(75) Inventors: Rodrigo Ayala, Milwaukee, WI (US); Bernice E. Hoppel, Delafield, WI (US)

(73) Assignee: General Electric Co., Schenectady, NY (US)

( * ) Notice: Subject to any disclaimer, the term of this patent is extended or adjusted under 35 U.S.C. 154(b) by 71 days.

(21) Appl. No.: 12/275,298

(22) Filed: Nov. 21, 2008

(65) Prior Publication Data

US 2010/0128838 A1 May 27, 2010

(51) Int. Cl.
 *A61B 6/03* (2006.01)
 *H05G 1/60* (2006.01)
(52) U.S. Cl. .................. 378/8; 378/15; 378/95
(58) Field of Classification Search ............ 378/8, 378/15, 20, 95
 See application file for complete search history.

(56) References Cited

U.S. PATENT DOCUMENTS

| | | | | |
|---|---|---|---|---|
| 5,278,884 A | * | 1/1994 | Eberhard et al. | 378/4 |
| 5,463,666 A | * | 10/1995 | Eberhard et al. | 378/4 |
| 6,061,420 A | * | 5/2000 | Strong et al. | 378/4 |
| 6,580,777 B1 | * | 6/2003 | Ueki et al. | 378/17 |
| 6,850,587 B1 | * | 2/2005 | Karimi et al. | 378/15 |
| 7,221,729 B2 | * | 5/2007 | Wakai et al. | 378/8 |
| 7,313,213 B1 | | 12/2007 | Hsieh et al. | |
| 7,313,215 B2 | | 12/2007 | Hsieh et al. | |
| 7,403,587 B2 | * | 7/2008 | Bontus et al. | 378/4 |
| 7,406,148 B2 | * | 7/2008 | Russinger et al. | 378/15 |
| 7,526,063 B2 | * | 4/2009 | Boing et al. | 378/8 |
| 7,616,730 B2 | * | 11/2009 | Flohr | 378/8 |
| 7,649,972 B2 | * | 1/2010 | Hagiwara et al. | 378/4 |
| 2008/0292045 A1 | * | 11/2008 | Iisaku et al. | 378/4 |
| 2009/0116717 A1 | * | 5/2009 | Kohler et al. | 382/131 |

FOREIGN PATENT DOCUMENTS

WO WO2007/113704 A2 * 10/2007

* cited by examiner

*Primary Examiner*—Allen C. Ho

(57) ABSTRACT

An method of computed tomography is disclosed herein. The method includes acquiring an axial dataset and acquiring a helical dataset as part of an acquisition protocol. A computed tomography system is also disclosed.

17 Claims, 4 Drawing Sheets

COMPUTED TOMOGRAPHY METHOD AND SYSTEM

FIELD OF THE INVENTION

This disclosure relates generally to a computed tomography method and system.

BACKGROUND OF THE INVENTION

Typically, in computed tomography (CT) systems, an x-ray tube emits a fan-shaped x-ray beam or a cone-shaped x-ray beam toward a patient positioned on a table. The x-ray beam, after being attenuated by the patient, impinges upon a detector assembly comprising a plurality of detector elements. The intensity of the attenuated x-ray beam received at the detector assembly is typically dependent upon the attenuation of the x-ray beam by the patient. Each detector element produces a separate electrical signal indicative of the intensity of the attenuated x-ray beam received at that particular detector element.

In known third generation CT systems, the x-ray source and the detector assembly are rotated on a gantry around the object to be imaged so that a gantry angle at which the fan-shaped or cone-shaped x-ray beam intersects the patient constantly changes. The table supporting the patient may be advanced while the gantry is rotating around the object being imaged. Data representing the intensity of the received x-ray beam at each of the detector elements is collected across a range of gantry angles. The data are ultimately reconstructed to form an image of the patient.

Third generation CT systems typically acquire data using either an axial acquisition mode or a helical acquisition mode. During an axial acquisition mode, the patient is stationary with respect to the rotating gantry while an axial dataset is acquired. During a helical acquisition mode, the patient is advanced with respect to the rotating gantry while a helical dataset is acquired.

Since the patient is not moving while the axial dataset is collected, it is possible to use a much simpler reconstruction algorithm to reconstruct an image from the axial dataset. Compared to an image reconstructed from the helical dataset, it may be possible to reconstruct an image with better resolution and fewer artifacts by using an axial dataset. However, when acquiring an axial dataset of an anatomical feature experiencing periodic motion, such as the heart, it is a standard practice to only acquire data during a specific portion of the periodic cycle. This is called prospective gating. Acquiring a prospectively gated axial dataset minimizes the patient's exposure to x-rays since the x-ray beam is only activated during a portion of the patient's periodic cycle.

The helical acquisition mode has a different set of strengths and weaknesses when compared to the axial acquisition mode. Since the table is moving during the helical acquisition, it is possible to cover more of the patient in a z-direction with a helical acquisition mode than with a single axial acquisition. Also, the helical acquisition mode accommodates a wider range of patients more easily. For example, it is difficult to accommodate patients with a highly variable heart rate using a conventional axial acquisition mode. It is also hard to acquire an axial dataset of the correct portion of the cardiac cycle if the patient experiences an irregular heartbeat. Since the helical acquisition mode is not prospectively gated, it easily accommodates both patients with variable heart rates and patients experiencing irregular heartbeats. However, since the helical acquisition mode is not prospectively gated, it may result in exposing the patient to a higher x-ray dose than a prospectively gated axial scan of the same anatomic region.

For these and other reasons, there is a need for an acquisition mode that addresses some of the limitations of the known axial acquisition mode and the known helical acquisition mode.

BRIEF DESCRIPTION OF THE INVENTION

The above-mentioned shortcomings, disadvantages and problems are addressed herein which will be understood by reading and understanding the following specification.

In an embodiment, a method of computed tomography includes acquiring an axial dataset as part of an acquisition protocol and acquiring a helical dataset as part of the acquisition protocol.

In an embodiment, a method of computed tomography includes acquiring an axial dataset of a patient, analyzing a patient parameter, and switching from acquiring the axial dataset to acquiring a helical dataset in response to the analyzing the patient parameter.

In an embodiment, a computed tomography system includes a gantry, an x-ray tube mounted to the gantry, a table adapted to translate with respect to the gantry, and a controller connected to the gantry, the x-ray tube and the table, wherein the controller is configured to acquire both an axial dataset and a helical dataset as part of the same acquisition protocol.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
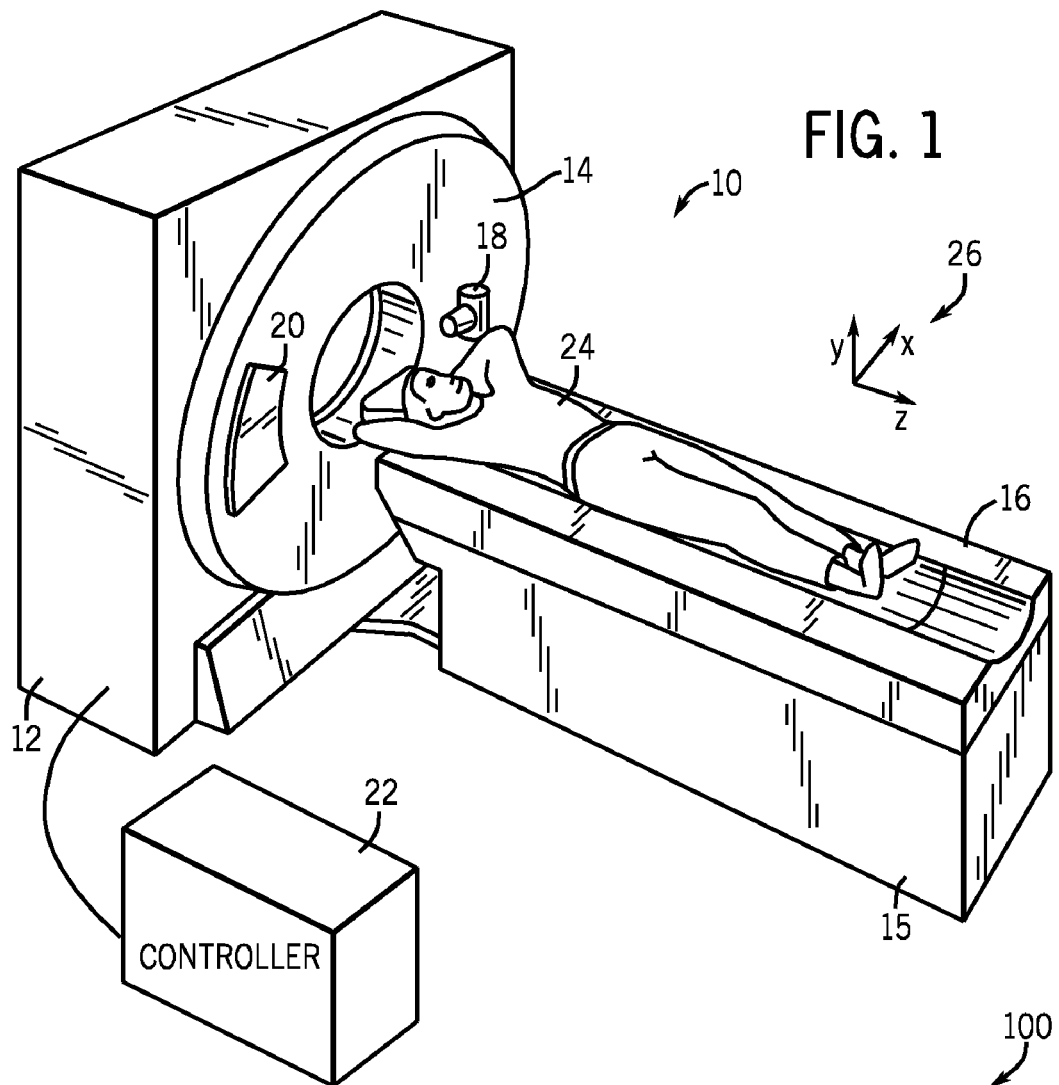
FIG. 1 is a schematic diagram illustrating a computed tomography system in accordance with an embodiment.

Referring to FIG. 1, a schematic representation of a computed tomography (CT) system 10 according to an embodiment is shown. The CT system 10 includes a gantry support 12, a gantry 14, a table support 15, a table 16, an x-ray tube 18, a detector assembly 20, and a controller 22. The gantry 14 is configured to rotate within the gantry support 12. The gantry 14 is adapted to retain the x-ray tube 18 and the detector assembly 20. The x-ray tube 18 is configured to emit an x-ray beam (not shown) towards the detector assembly 20. The detector assembly 20 comprises a plurality of detector elements (not shown). Each of the plurality of detector elements (not shown) produces an electrical signal that varies based on the intensity of the x-ray beam (not shown) received during a sampling interval. The table 16 is adapted to translate the patient 24 in a z-direction with respect to the gantry 14 as indicated by a coordinate axis 26. The controller 22 is configured to control the rotation of the gantry 14, the position of the table 16, and the activation of the x-ray tube 18.

Figure 2:
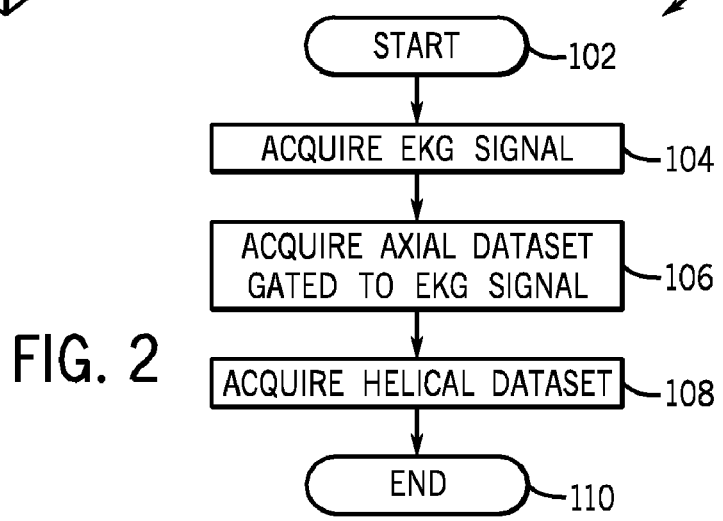
FIG. 2 is a flow chart illustrating a method in accordance with an embodiment.

FIG. 2 is a flow chart illustrating a method 100 in accordance with an embodiment. The individual blocks 102-110 represent steps that may be performed in accordance with the method 100. The steps need not be performed in the order shown. The technical effect of the method 100 is the acquisition of an axial dataset and a helical dataset.

Referring to FIG. 1 and FIG. 2, the method 100 starts at step 102. At step 104, a patient monitoring system (not shown) acquires an EKG signal. The EKG signal is transmitted from the patient monitoring system (not shown) to the controller 22. At step 106, the method 100 acquires an axial dataset that is gated to the EKG signal. For example, according to an embodiment, the axial dataset is acquired only during a particular portion of the patient's cardiac cycle. For the purposes of this disclosure, the term axial dataset includes a computed tomography dataset that is acquired while the patient 24 is stationary with respect to the rotating gantry 14. Hereinafter, for the purposes of this disclosure, it should be understood that an axial acquisition mode is used to acquire an axial dataset. According to an embodiment shown in FIG. 1, the patient 24 is kept stationary with respect to the gantry support 12 and the rotating gantry 14 while the axial dataset is being acquired at a specific location. In order to acquire the axial dataset, the x-ray tube 18 emits a cone beam of x-rays that is detected by the detector assembly 20. According to another embodiment, step 104 may be replaced with a step where another physiological signal, such as a respiratory signal, is acquired. Also, step 106 may be replaced by a step where an axial dataset is acquired that is gated to a physiological signal other than an EKG signal. According to one exemplary embodiment, the acquisition of the axial dataset may occur while gated to a respiratory signal.

At step 108, the method 100 acquires a helical dataset. For the purposes of this disclosure, the term "helical dataset" includes a dataset that is acquired while the patient 24 is translated with respect to the rotating gantry 14. Hereinafter, for the purposes of this disclosure, it should be understood that a helical acquisition mode is used to acquire the helical dataset. According to the embodiment shown in FIG. 1, the patient is translated in the z-direction by the table 16 while the gantry 14 rotates. As the gantry 14 rotates, the x-ray tube 18 emits a cone beam of x-rays that is detected by the detector assembly 20. The helical dataset may be acquired according to other methods according to other embodiments.

Both the axial dataset acquired during step 106 and the helical dataset acquired during step 108 are acquired as part of the same acquisition protocol. For the purposes of this disclosure, the term acquisition protocol includes a set of commands that are followed in order to collect one or more computed tomography datasets. Both the axial dataset and the helical dataset are examples of computed tomography datasets. In order to be considered as part of the same acquisition protocol, the acquisition of the axial dataset and the helical dataset must occur without additional input from an operator. Additionally, there may be a short time differential between acquiring the axial dataset during step 106 and acquiring the helical dataset during step 108. For example, according to an embodiment, the time differential between the end acquiring the axial dataset at step 106 and the beginning of acquiring the helical dataset at step 108 may be 60 seconds or less. It should be appreciated, that according to other embodiments, a helical dataset may be acquired before an axial dataset is acquired. According to these embodiments, the time differential between the end of acquiring the helical dataset and the beginning of acquiring the axial dataset may be 60 seconds or less. At step 110, the method 100 ends.

According to an embodiment, an image may be created using both the helical dataset and the axial dataset. Creating an image may comprise reconstructing a first image from the axial dataset, reconstructing a second image from the helical dataset, and then displaying at least a portion of the first image and at least a portion of the second image. According to another embodiment, creating an image may comprise using information in either the helical dataset or the axial dataset to help register two or more images as will be discussed in detail hereinafter. According to another embodiment, creating an image may comprise using information in the helical dataset in order to improve the image quality of an image that is reconstructed from the axial dataset. For example, this may comprise using projections from the helical dataset in order to reduce artifacts in an image reconstructed from the axial dataset. It should be appreciated by those skilled in the art, that embodiments may comprise additional ways of using information in both the axial dataset and the helical dataset to create an image that may be analyzed and/or displayed.

Figure 3:
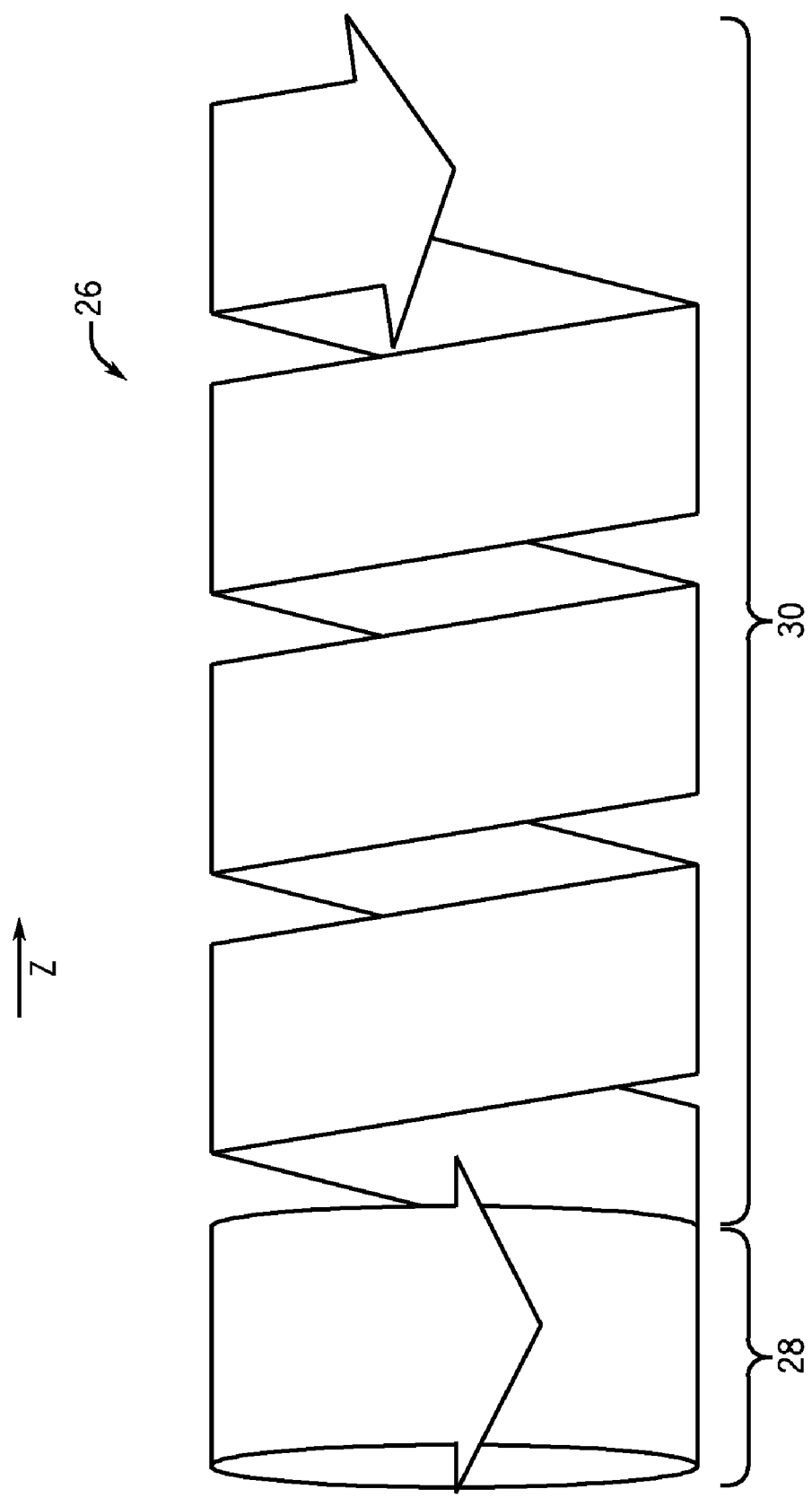
FIG. 3 is a schematic diagram illustrating a path of an x-ray tube in accordance with an embodiment.

In FIG. 3, a schematic representation of a path 26 of the x-ray tube 18 (shown in FIG. 1) with respect to the patient 24 (shown in FIG. 1) according to the method 100 (shown in FIG. 2) is shown.

Referring now to FIG. 1, FIG. 2, and FIG. 3, at step 106 when the axial dataset is being acquired, the x-ray source 18 traces a circular path 28 around the patient 24. The table 16 is stationary with respect to the rotating gantry 14 during step 106. During step 108, the x-ray source 18 traces a helical path 30 with respect to the patient 24. During step 108, the table 16 is translated with respect to the rotating gantry 14 while the helical dataset is being acquired.

Figure 4:
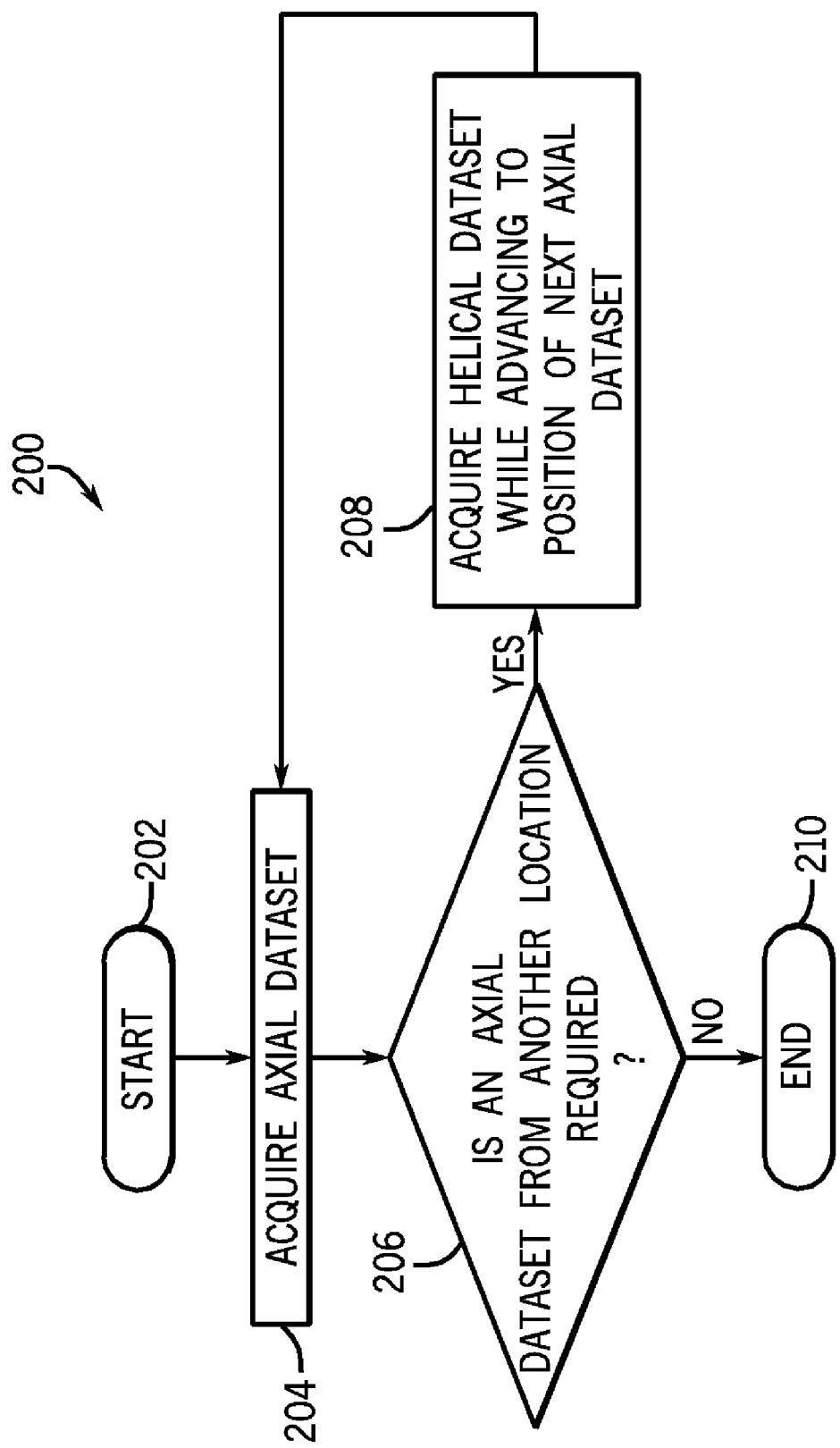
FIG. 4 is a flow chart illustrating a method in accordance with an embodiment.

FIG. 4 is a flow chart illustrating a method 200 in accordance with an embodiment. The individual blocks 202-210 represent steps that may be performed in accordance with the method 200. The steps need not be performed in the order shown. The technical effect of the method 200 is the acquisition of at least one axial dataset and at least one helical dataset.

Referring to FIG. 1 and FIG. 4, at step 202, the method 200 starts. At step 204, the controller 22 acquires an axial dataset while the CT system 10 is in an axial acquisition mode. After the axial dataset has been acquired, the method 200 advances to step 206, where the controller 22 determines if an axial dataset from another location is required. If an axial dataset is required from another location, the method 200 advances to step 208. According to an embodiment, the controller 22 may determine if another axial dataset is required from another location while acquiring an axial dataset.

At step 208, the controller 22 acquires a helical dataset while the CT system 10 is in a helical acquisition mode. According to an embodiment, the x-ray source 18 may stay in an active state while the method 200 transitions between acquiring the axial dataset at step 204 and acquiring the helical dataset at step 208. According to another embodiment, there may be a time differential of up to 60 seconds between the end of acquiring the axial dataset at step 204 and the beginning of acquiring the helical dataset at step 208. The controller 22 continues acquiring the helical dataset until the patient has been advanced to the position of the next axial dataset. Once the patient 24 has reached the position of the next axial dataset, the controller 22 stops acquiring the helical dataset.

After the helical dataset has been acquired at step 208, the method returns to step 204. At step 204, an axial dataset is acquired at the new position. It should also be understood that the time differential from the end of acquiring the helical dataset at step 208 to the beginning of acquiring the axial dataset during step 204 could also vary between 0 and 60 seconds depending on the embodiment. The method 200 iteratively cycles through steps 204-208 until the controller 22 determines that no additional axial datasets are required at step 206. If no additional axial datasets are required at step 206, the method 200 advances to step 210 and the method 200 ends.

Still referring to FIG. 1 and FIG. 4, the method 200 may be used to image a patient's heart. According to an embodiment, all of the axial datasets are prospectively gated to the patient's cardiac cycle using a conventional technique that is well-known to those skilled in the art. According to an exemplary embodiment, it may take 4 axial datasets at separate locations to completely image the patient's heart. The patient 24 may be positioned so that each subsequent axial dataset is adjacent to the previous axial dataset without any overlap. According to other embodiments, the axial datasets may partially overlap each other or the axial datasets may be separated by a distance in the z-direction.

Still referring to FIG. 4, according to an embodiment, the axial datasets may be acquired at step 204 using an x-ray beam created with an x-ray tube current level of approximately 600 mA. The helical datasets may be acquired using an x-ray beam created with an x-ray tube current level of approximately 300 mA. The higher x-ray tube current level may allow the axial datasets to be of a higher resolution than the helical datasets. It should be appreciated, that the x-ray tube current levels used to create the x-ray beams for acquiring the axial datasets and the helical datasets may be of different values according to other embodiments. For example, according to an embodiment, the axial datasets may also be acquired using an x-ray beam created from an x-ray tube current level selected from the range of 500 mA to 800 mA, and the helical datasets may be acquired using an x-ray beam created from an x-ray tube current level selected from the range of 200 mA to 500 mA. It should be appreciated that embodiments may acquire different numbers of axial datasets and helical datasets depending upon the size of the volume of interest and the specific design of the CT system being used.

Still referring to FIG. 1 and FIG. 4, according to an exemplary embodiment, the datasets acquired during the method 200 may all be acquired as part of a single translational pass of the table 16 with respect to the gantry 14. For the purposes of this disclosure, the term single translational pass includes methods where the relative motion between the table 16 and the gantry 14 occurs in only a single direction. For example, the table 16 is stationary while the axial dataset is acquired at step 204. Then, at step 208, the table 16 may be translated in either the positive z-direction or the negative z-direction depending on the embodiment. When the method 200 returns to step 204, the table 16 is stationary while the next axial dataset is acquired. Then, if an additional helical dataset is required, the table 16 may be moved in the same direction at step 208 as it was when the previous helical dataset was acquired. In other words, if the table 16 was translated in the positive z-direction while acquiring a first helical dataset, the second helical dataset may also be acquired while translating the table 16 in the positive z-direction. According to another embodiment, if the table 16 was translated in the negative z-direction while acquiring a first helical dataset, any additional datasets, such as the second helical dataset, may be acquired while translating the table 16 in the negative z-direction.

According to an embodiment, the axial datasets may be prospectively gated to a cardiac cycle of a patient. This means that the axial datasets only contain information about a portion of the cardiac cycle. However, the helical datasets are not prospectively gated to the cardiac cycle. This means that the helical datasets contain information about all portions of the cardiac cycle, including portions that were not captured by the axial datasets. According to an embodiment, the helical datasets may be used to provide information that is not available in the axial datasets. Even if the helical datasets are of a lower resolution than the axial datasets, the helical datasets may still be used to obtain quantitative information about an organ or to provide additional images that would not otherwise be available. A non-limiting list of quantitative information that may be obtained by using the helical dataset includes cardiac wall motion, wall thickness, ejection fraction, and total volume. It should be understood that the axial datasets may be gated to physiological cycles other than the cardiac cycle according to an embodiment.

According to an embodiment, a helical dataset that overlaps with both a first axial dataset and a second axial dataset may be used to effectively register an image reconstructed from the first axial dataset to an image reconstructed from the second axial dataset. By registering the images, it may be possible to minimize any artifacts due to motion occurring between the acquisition of the first axial dataset and the acquisition of the second axial dataset. Since reconstructing an image from an axial dataset may not require the interpolation of any data, it may by possible to reconstruct an image with fewer artifacts compared to an image reconstructed from a helical dataset. Since, according to an embodiment, the helical dataset/s will not be used to reconstruct a final image, the helical dataset/s do not need to contain information at as high of a resolution. For example, the axial dataset/s may be acquired at an x-ray tube current level from the range of 500 mA to 800 mA, while the helical dataset/s may be acquired at an x-ray tube current level from the range of 200 mA to 500 mA. Since the axial dataset/s are acquired at a higher x-ray tube current level, higher resolution images may be reconstructed from the axial datasets. Since the helical dataset/s are acquired from a lower x-ray tube current level, the patient's exposure to x-ray radiation is minimized while the helical dataset/s still provide the benefit of providing additional information and reducing artifacts.

An embodiment may be used to acquire information about an anatomical region that is longer in the z-direction than the width of the detector assembly 20 (shown in FIG. 1). For example, an exemplary embodiment may be used to perform a run-off study involving a contrast agent. When performing a run-off study, the timing of the acquisition is critical in order to ensure that a bolus of the contrast agent provides maximum contrast. If the acquisition is too early, the bolus will not have arrived yet and there will be no improvement in contrast. If the acquisition is too late, the bolus will have passed and the contrast will not be optimal. Additionally, when performing a run-off study, there is a desire to have high resolution images of areas where there are a large number of bifurcations in the blood vessels, such as around the kidneys, the knees, and the ankles. However, there is not a need for high resolution images for areas without a large number of bifurcations; such as a portion of the leg between the kidney and the knee, and a portion of the leg between the knee and the ankle.

According to an exemplary embodiment, the patient is injected with a contrast agent. Then, a low-dose helical acquisition mode is used to track the contrast bolus. The helical acquisition mode is performed using an x-ray beam created by an x-ray tube current level of approximately 200 mA and results in the acquisition of a low-dose helical dataset. When the contrast bolus reaches the kidneys, one or more higher resolution axial datasets are acquired of the kidney region. The axial dataset of the kidney region is acquired using an x-ray beam created by an x-ray tube current level of approximately 600 mA. A second low-dose helical dataset is acquired while tracking the contrast from the kidney region to the knee region. Once the bolus has reached the knee region, one or more higher resolution axial datasets are acquired of the knee region. Then, a third low-dose helical dataset is acquired while tracking the contrast from the knee region to the ankle region. Once the bolus has arrived at the ankle, one or more axial datasets are acquired of the ankle region. It should be appreciated that the axial datasets and the helical datasets may be acquired using x-ray beams created by x-ray tube current levels other than those described in this exemplary embodiment.

It should be appreciated, that according to additional embodiments, an axial dataset could be acquired for any region of the body when a higher resolution image is desired and the acquisition of a helical dataset could be used for any area when a higher resolution image is not desired. It should also be understood that according to other embodiments, a helical dataset may have a resolution that is as high or higher than an axial dataset.

Figure 5:
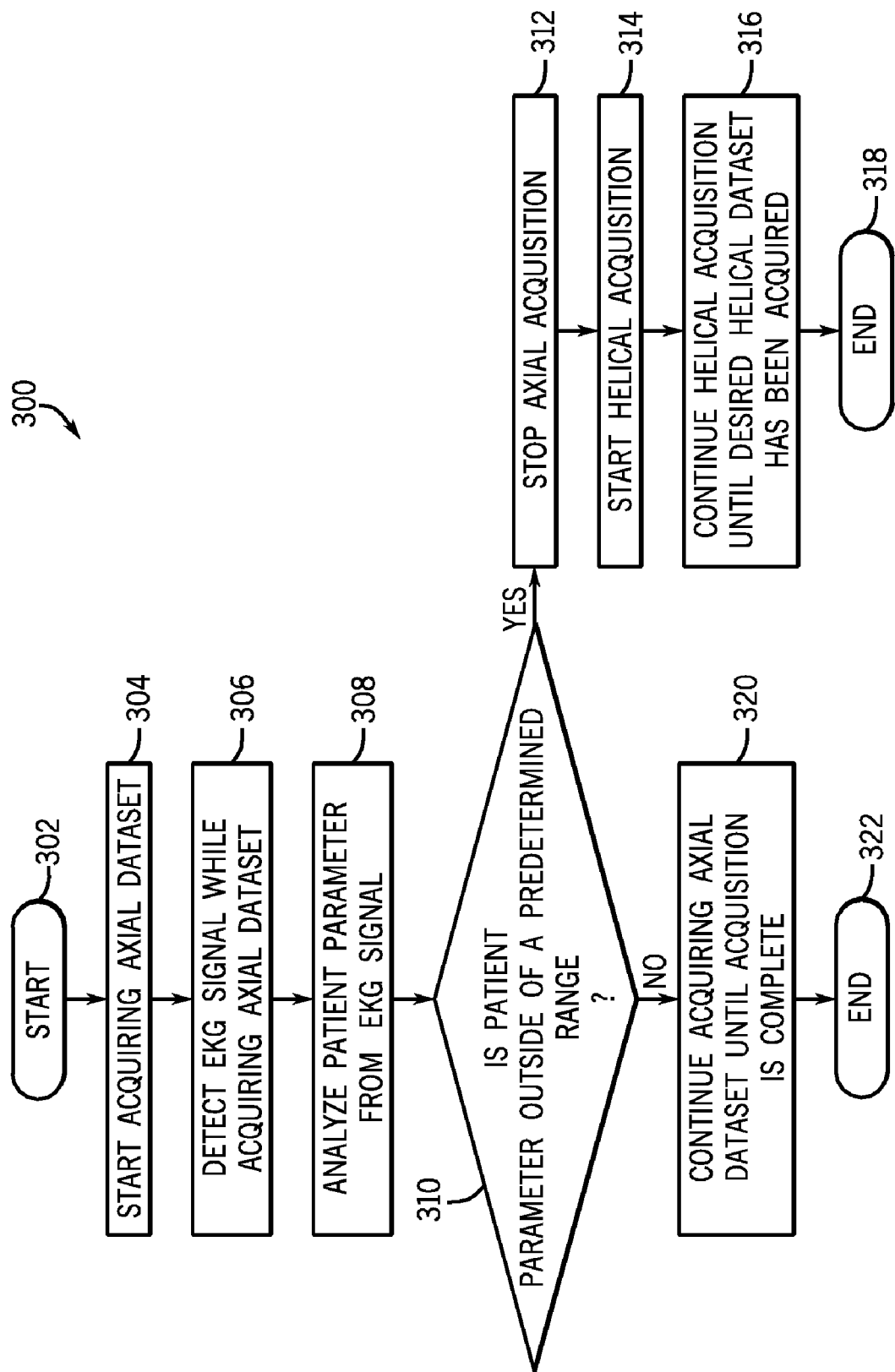
FIG. 5 is a flow chart illustrating a method in accordance with an embodiment.

FIG. 5 is a flow chart illustrating a method 300 in accordance with an embodiment. The individual blocks 302-322 represent steps that may be performed in accordance with the method 300. The steps need not be performed in the order shown. The technical effect of the method 300 is the acquisition of at least one axial dataset and at least one helical dataset.

Referring to FIG. 5, at step 302, the method 300 starts. At step 304, the method starts acquiring an axial dataset that is gated to a physiological signal from the patient. According to an embodiment, the axial dataset may be gated to an EKG signal. According to additional embodiments, the axial dataset could be gated to other physiological signals as well, such as a respiratory signal. At step 306, the method 300 detects an EKG signal while acquiring the axial dataset. At step 308, a patient parameter, such as, for example, a heart rate is analyzed from the EKG signal. Other patient parameters, either from the EKG signal or from other sources, may be analyzed as well. According to additional embodiments, an EKG complex may be analyzed determine if a patient has experienced an irregular heart beat or a respiratory rate may be analyzed to determine if a patient is breathing within a predetermined range.

At step 310, the method 300 determines if the patient parameter is outside of a predetermined range. According to an exemplary embodiment, the method 300 may determine if the heart rate is outside of a predetermined range. For example, according to an embodiment, if the heart rate is above 100 beats per minute, it may be considered to be outside of the predetermined range. If the patient parameter is outside of the predetermined range, the method 300 proceeds to step 312, where the axial acquisition is stopped. Next, at step 314, a helical acquisition is started. According to an exemplary embodiment, the helical acquisition captures data for all portions of a cardiac cycle while the axial acquisition only captures data for a portion of the cardiac cycle. Since the helical acquisition captures data for all portions of the cardiac cycle, it is a more-reliable way to acquire data if the patient parameter is found to be outside of the predetermined range during step 310. At step 316, the helical acquisition is continued until the helical dataset includes the entire volume of interest. Then, the method 300 ends at step 318.

Still referring to FIG. 5, at step 310, if the patient parameter is found to be within the predetermined range, the method 300 proceeds to step 320. At step 320, the method 300 continues acquiring the axial dataset until the acquisition is complete. Then the method 300 advances to step 322 and ends after the axial dataset has been acquired. It should be appreciated that, according to an embodiment, more than one axial dataset may be acquired if additional axial datasets are required to completely cover the volume of interest and the patient parameter remains within the predetermined range. However, if the patient parameter is found to be outside of the predetermined range during the acquisition of one of the additional axial datasets, the method would stop acquiring the additional axial dataset and switch to acquiring a helical dataset, in a manner similar to that described during steps 312-318 of the method 300.

According to an embodiment, if more than one axial dataset are required to cover a volume of interest, a helical dataset may be acquired while moving from the position of one axial acquisition to the position of the next axial acquisition in a manner similar to that described in the method 200 (shown in FIG. 4). However, if the patient parameter is detected to be outside of a predetermined range, an embodiment may stop the axial acquisition and start a helical acquisition in a manner similar to that described in steps 312-318 of the method 300 (shown in FIG. 5).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of computed tomography comprising:
   acquiring an axial dataset as part of an acquisition protocol;
   acquiring a helical dataset as part of said acquisition protocol;
   reconstructing an image from the axial dataset, the image comprising a first portion of a cardiac cycle: and
   reconstructing a second image from the helical dataset. the second image comprising a second portion of the cardiac cycle that differs from the first portion of the cardiac cycle.

2. The method of claim 1, wherein the axial dataset is gated to a physiological signal.

3. The method of claim 1, wherein said acquiring the axial dataset comprises acquiring the axial dataset at a first x-ray tube current level.

4. The method of claim 3, wherein said acquiring the helical dataset comprises acquiring the helical dataset at a second x-ray tube current level that is different from the first x-ray tube current level.

5. The method of claim 4, wherein the second x-ray tube current level is lower than the first x-ray tube current level.

6. The method of claim 1, further comprising creating an image using both the axial dataset and the helical dataset.

7. The method of claim 1, wherein said acquisition protocol comprises a time differential of 60 seconds or less between said acquiring the axial dataset and said acquiring the helical dataset.

8. The method of claim 1, wherein said acquisition protocol comprises a time differential of 10 seconds or less between said acquiring the axial dataset and said acquiring the helical dataset.

9. A method of computed tomography comprising:
acquiring an axial dataset of a patient;
comparing a heart rate to a predetermined range; and
switching from said acquiring the axial dataset to acquiring a helical dataset in response to said comparing the heart rate to the predetermined range.

10. The method of claim 9, further comprising using both the axial dataset and the helical dataset to create an image of the patient.

11. A method of computed tomography comprising:
acquiring an axial dataset of a patient;
determining that a patient's heart beat is irregular; and
switching from said acquiring the axial dataset to acquiring a helical dataset in response to said determining that the patient's heart beat is irregular.

12. The method of claim 11, further comprising using both the axial dataset and the helical dataset to create an image of the patient.

13. A computed tomography system comprising:
a gantry;
an x-ray tube mounted to the gantry;
a detector assembly mounted to the gantry, the detector assembly comprising a plurality of detector elements that produce electric signals in response to an x-ray beam;
a table adapted to translate with respect to the gantry; and
a controller connected to the gantry, the x-ray tube, the detector assembly, and the table;
wherein the controller is configured to receive a patient's heart rate from a patient monitoring system, the controller configured to analyze the patient's heart rate, the controller configured to switch from acquiring an axial dataset to acquiring a helical dataset of the patient in response to determining that the patient's heart rate is outside of a predetermined range.

14. The computed tomography system of claim 13, wherein the controller is further configured to acquire the axial dataset using a first x-ray tube current level and acquire the helical dataset using a second x-ray tube current level.

15. The computed tomography system of claim 13, wherein the controller is further configured to create an image using both the helical dataset and the axial dataset.

16. The computed tomography system of claim 13, wherein the controller is further configured to use the helical dataset to reduce an artifact due to motion.

17. The computed tomography system of claim 13, wherein the controller is configured to acquire the axial dataset and the helical dataset as part of a single translational pass of the table with respect to the gantry.

* * * * *